United States Patent [19]

Kelley

[11] Patent Number: 5,437,869

[45] Date of Patent: Aug. 1, 1995

[54] PEST CONTROL SYSTEM

[76] Inventor: Donald W. Kelley, 6205 Glenmoor Ave., Garland, Tex. 75043

[21] Appl. No.: 968,997

[22] Filed: Oct. 29, 1992

Related U.S. Application Data

[63] Continuation-in-part of Ser. No. 782,512, Oct. 24, 1991, abandoned.

[51] Int. Cl.⁶ ............................................. A01N 25/32
[52] U.S. Cl. ................................. 424/406; 424/409; 424/411
[58] Field of Search ................. 424/411, 408, 406, 409

[56] References Cited

U.S. PATENT DOCUMENTS

| | | |
|---|---|---|
| 3,944,662 | 3/1976 | Miller, Jr. et al. ................. 424/78 |
| 3,973,035 | 8/1976 | Searle et al. ....................... 424/304 |
| 4,150,109 | 4/1979 | Dick et al. ........................... 424/28 |

FOREIGN PATENT DOCUMENTS

| | | | |
|---|---|---|---|
| 0167726 | 1/1986 | European Pat. Off. ............ 424/411 |
| 2111830 | 7/1983 | United Kingdom ................ 424/411 |
| 2169805 | 7/1986 | United Kingdom ................ 434/411 |

OTHER PUBLICATIONS

Zhang, Kunchongxue Yanjiu Jikan, 6, 109–14, 1986, CA 108(13):108096y, "Further Investigations of Synergist and Cross Resistance to Non–Pyrethroids is Resmethrin–Selected Mosquitoes, Culex Pipiens Pallens Coq".

*Primary Examiner*—Thurman K. Page
*Assistant Examiner*—Neil Levy
*Attorney, Agent, or Firm*—Donald W. Erickson

[57] ABSTRACT

A solid pest control system which includes a polymeric matrix, a liquid plasticizer, a pest control active ingredient and triphenyl phosphate as a carrier for the active ingredient. The system releases the active ingredient efficiently and uniformly. The pest control system is less irritating to the animal's skin as compared to prior art systems. The system is useful for making animal collars, ear tags, pest strips, and the like. The irritation of pest control active ingredient to warm blooded animals, including humans, is reduced by incorporating into the active ingredient formulation an effective amount of triphenyl phosphate. The formulation can be a solid or liquid.

12 Claims, No Drawings

PEST CONTROL SYSTEM

This is a continuation-in-part of Ser. No. 07/782,512, filed Oct. 24, 1991, now abandoned, the entire disclosure of which is incorporated herein.

BACKGROUND OF THE INVENTION

Pest control active ingredients have been and are currently blended with polymers such as polyvinyl chloride and then shaped into forms such as strips, animal collars and animal ear tags for use in controlling pests. See, for example, U.S. Pat. Nos. 3,318,769, 3,852,416 and 4,150,109. A principle disadvantage of the prior art polymer/active ingredient blends is that a considerable amount of the active ingredient is not released by the blend and is unavailable for the control of the target pest. This factor reduces the cost effectiveness and useful life of the product. Another disadvantage of prior art polymer/active ingredient blends is that the rate of release of active ingredient from the blends not uniform which results in less efficient use of the active ingredient. The present invention overcomes the aforementioned drawbacks of the prior art blends (systems).

Many pest control active ingredients are irritants to warm blooded animals (including humans). This irritation to the skin and/or eyes of warm blooded animals hampers the use of pest control active ingredients. This irritation factor occurs even when the pest control active ingredient is blended with polymers or, in other formulations, such as granules, dusts, dips, liquids, emulsions, etc., wherein the active ingredient is considerably diluted. The present invention overcomes or significantly reduces the irritation to warm blooded animals of pest control ingredients.

SUMMARY OF THE INVENTION

A system for the controlled release of a pest control active ingredient (AI) or a mixture of active ingredients from a polymer matrix that is more efficient in releasing the active ingredient(s) than prior art systems (blends). In addition, the pest control systems of the present invention have a uniform rate of release of the active ingredient which makes for more effective and efficient use of the active ingredient. The systems employ a vinyl polymer such as polyvinyl chloride (PVC) which is loaded with a highly solvating plasticizer and triphenyl phosphate (TPP) as the active ingredient carrier.

A method and composition in accordance with the present invention reduces the irritation of an AI to warm blooded animals (including humans). The irritation of an AI to the skin and/or eyes of warm blooded animals is reduced by incorporating into the AI formulation an effective amount of TPP. These formulations may be solid such as a polymer, granule or dust, liquids such as a dip or a spot-on, or an emulsion. This invention is, particularly, useful for reducing the irritation of natural pyrethrins and synthetic pyrethroids to warm blooded animals. It is effective without loss of the biological activity of the AI such as natural pyrethrins and synthetic pyrethroids.

DETAILED DESCRIPTION OF THE INVENTION

In the practice of the present invention, in the preferred embodiment, polyvinyl chloride, or other vinyl polymer, as a dry blend resin is loaded with highly solvating plasticizer(s) such as dioctyl adipate. The amount of plasticizer used is the maximum amount possible and still maintain a dry and flowable blend. Separately, the active ingredient is blended with the solid active ingredient carrier (triphenylphosphate) at a predetermined ratio to form the AI Carrier blend. This blend is then melted and made homogenous by thorough blending, cooled back to a solid which is ground into small particles. Then the resin blend and the active ingredient blend are mixed together at a predetermined ratio. The resulting blend is then processed by mixing in a heated plastic state and extruded into the desired physical shape.

At processing temperatures the AI Carrier blend is much less compatible with the polymer than the plasticizer but is compatible enough at the elevated temperatures that it is dispersed within the polymer/plasticizer blend much like a micro-emulsion. Without being bound by theory, it is believed that when the total blend cools, the AI Carrier (TPP) becomes incompatible with the polymer while the plasticizer remains compatible with the polymer. As the AI Carrier blend recrystallizes or becomes solid, the plasticizer/polymer matrix acts as a particle size regulator by preventing the AI Carrier's crystalline structure from becoming large enough to be trapped within the matrix. Instead the crystals are small and are allowed to move within and out of the plasticized polymer matrix. The AI Carrier blend moves to the surface of the polymer matrix independent of the AI Carrier/active ingredient ratios so long as the amount of active ingredient does not exceed that of the AI Carrier or that enough of a liquid active ingredient is not used that would render the final AI Carrier/active ingredient blend less than a solid. Thus, much lower percentages of an active ingredient may be used and effectively released by having a high ratio of AI Carrier to the active ingredient in the systems (blends) of the present invention. This property allows high cost active ingredients to be used in market competitive products which use a lower cost active ingredient.

By loading the polymer with high levels of a solvating plasticizer, the polymer is unable to bind the AI Carrier/active ingredient blend to itself, leaving the blend free to move within the polymer matrix. This allows the active ingredient to be effectively released at much higher percentages than when the active ingredient is not prevented from becoming compatible with the polymer.

By combining TPP (AI carrier) with the AI (pest control active ingredient), the irritation to the skin and/or eyes of the AI to warm blooded animals (including humans) is reduced. This property of the present invention is particularly useful for reducing the irritation of natural pyrethrins and synthetic pyrethroids to warm blooded animals. The amount of TPP in the formulation relative to the amount of AI in order to obtain the benefits of the present invention is easily determinable by routine experimentation. Generally, the amount of TPP in the formulation should be at least equal to the amount of AI and, more usually, the amount of TPP in the formulation is double to several fold the amount of AI in the formulation in order to reduce the irritation value of the AI. The present invention applies to formulations that are solid such as polymer blends, granules and dusts, liquids such as a dip, spot-on or spray and emulsions. The anti-irritant property of the present invention is believed to be achieved by the physical combination of the AI Carrier and the active ingredient. As the AI Carrier crystallizes, it covers in part or totally the active ingredient making it less available to the animals' skin.

TABLE 1

| DOG ID NO. | Number of Fleas Counted on Each Dog at Indicated Days |  |  |  |  |  |  |  |  |  |  |  |  |  |  |  |  |
|---|---|---|---|---|---|---|---|---|---|---|---|---|---|---|---|---|---|
|  | Day |  |  |  |  |  |  |  |  |  |  |  |  |  |  |  |  |
|  | 0 | 1 | 3 | 7 | 9 | 14 | 16* | 209 | 211 | 216 | 218 | 223 | 225 | 230 | 232 | 237 | 239 |
| Untreated Control |  |  |  |  |  |  |  |  |  |  |  |  |  |  |  |  |  |
| 1 | 40 | 41 | 45 | 39 | 35 | 40 | 39 | 55 | 50 | 57 | 55 | 49 | 46 | 57 | 54 | 36 | 39 |
| 2 | 33 | 30 | 31 | 52 | 57 | 49 | 48 | 30 | 29 | 36 | 37 | 27 | 24 | 39 | 44 | 51 | 45 |
| 3 | 25 | 26 | 21 | 47 | 45 | 51 | 53 | 24 | 28 | 19 | 20 | 16 | 15 | 31 | 32 | 24 | 25 |
| Mean | 32.7 | 32.3 | 32.3 | 46.0 | 45.7 | 46.7 | 46.7 | 36.3 | 35.7 | 37.3 | 37.3 | 30.7 | 28.3 | 42.3 | 43.3 | 37.0 | 36.3 |
| Collared Dogs |  |  |  |  |  |  |  |  |  |  |  |  |  |  |  |  |  |
| 4 | 11 | 14 | 8 | 11 | 2 | 6 | 7 | 5 | 0 | 4 | 0 | 1 | 0 | 2 | 0 | 3 | 1 |
| 5 | 29 | 15 | 9 | 2 | 0 | 0 | 0 | 2 | 0 | 3 | 0 | 3 | 1 | 6 | 0 | 5 | 0 |
| 6 | 37 | 4 | 2 | 0 | 0 | 0 | 0 | 3 | 0 | 7 | 2 | 8 | 2 | 7 | 1 | 11 | 4 |
| Mean | 25.7 | 11.0 | 6.3 | 4.3 | 0.7 | 2.0 | 2.3 | 3.3 | 0.0 | 4.7 | 0.7 | 4.0 | 1.0 | 5.0 | 0.3 | 6.3 | 1.7 |
| Percent Reduction |  | 66 | 80 | 91 | 98 | 96 | 95 | 91 | 100 | 87 | 98 | 87 | 96 | 88 | 99 | 83 | 95 |

| DOG ID NO. | Day |  |  |  |  |  |  |  |  |  |  |  |
|---|---|---|---|---|---|---|---|---|---|---|---|---|
|  | 248 | 250** | 252 | 254 | 256 | 258 | 260 | 262 | 264 | 266 | 268 | 270 |
| Untreated Control |  |  |  |  |  |  |  |  |  |  |  |  |
| 1 | 51 | 46 | 24 | 31 | 39 | 43 | 32 | 29 | 47 | 42 | 28 | 34 |
| 2 | 31 | 29 | 62 | 67 | 42 | 40 | 58 | 55 | 25 | 30 | 22 | 25 |
| 3 | 38 | 40 | 47 | 44 | 69 | 67 | 34 | 39 | 51 | 52 | 43 | 46 |
| Mean | 40.0 | 38.3 | 44.3 | 47.3 | 50.0 | 50.0 | 41.3 | 41.0 | 41.3 | 41.3 | 31.0 | 35.0 |
| Collared Dogs |  |  |  |  |  |  |  |  |  |  |  |  |
| 4 | 10 | 2 | 7 | 3 | 12 | 5 | 12 | 4 | 8 | 5 | 20 | 9 |
| 5 | 4 | 3 | 4 | 1 | 8 | 2 | 6 | 2 | 9 | 1 | 11 | 5 |
| 6 | 16 | 4 | 13 | 9 | 14 | 5 | 10 | 8 | 15 | 5 | 13 | 7 |
| Mean | 10.0 | 3.0 | 8.0 | 4.3 | 11.3 | 4.0 | 9.3 | 4.7 | 10.7 | 4.7 | 14.7 | 7.0 |
| Percent Reduction | 75 | 92 | 82 | 91 | 77 | 92 | 77 | 89 | 74 | 91 | 53 | 80 |

*Days 21 to 204 the percent reduction ranged from 98% to 100%
**Collar removed from each dog.

However, due to the particle size regulating effect of the system of the present invention, the particle size is small enough to be effective against the targeted pest. Another benefit of the combination of TPP and active ingredient is that the blend thereof demonstrates an affinity for the animals' hair and that the crystals or particles adhere or stick to the animals' hair. Thus, in the case of a collar or ear tag, the biological activity of the AI continues for days and weeks after the collar or tag has been removed.

EXAMPLE 1

Dog collars were made from the following formulation (percent by weight) using the procedure described above.

| | |
|---|---|
| PVC (med. mol. wt.) | 40.6 |
| Stabilizer (CZ19A) | 0.4 |
| Epoxidized oil | 5.0 |
| Dioctyl adipate | 18.0 |
| Triphenyl phosphate | 32.0 |
| Tralomethrin dust (63.5%) | 4.0 |

Collars measuring about 0.375 inches wide, about 0.125 inches thick and about 20 inches long were made for evaluation of ectoparasite mortality on dogs. Two groups of 3 dogs per group were housed individually in concrete floored pens which were cleaned daily. Three dogs were used as untreated controls and three dogs were fitted with collars made with the formulation of Example 1. The day before fitting three of the dogs with a collar, each of the six dogs was infected by placing 100 unfed adult fleas (Ctenocephalides felis) along the dorsal midline from its head to the base of its tail. Each dog was reinfected on a weekly basis.

As Shown in Table 1, the collars were removed on Day 250. Very effective flea mortality, nevertheless, continued through Day 270 (80% reduction) when the test was stopped. Dogs from which the collar was removed on Day 250 showed very effective tick mortality through Day 270 (83% reduction) when the test was stopped.

EXAMPLE 2

The following formulations 2A, 2B and 2C were prepared and formed into dog collars using the procedure of Example 1 (percentage by weight).

| Formulation | | |
|---|---|---|
| 2A | PVC (med. mol. wt.) | 43.5 |
|  | Stabilizer (Witco CZ19A) | 0.5 |
|  | Epoxidized oil | 5.0 |
|  | Dioctyl adipate | 18.0 |
|  | TPP | 31.0 |
|  | Tralomethrin dust (63.5%) | 2.0 |
| 2B | Same as formulation 2A except used 30.3 TPP and 2.7 tralomethrin (TLM). | |
| 2C | Same as formulation 2A except used 29.0 TPP and 4.0 TLM. | |

Three groups of dogs, 3 each group, were fitted with collars made of formulation 2A, 2B and 2C. Each dog in one group was fitted with four collars of formulation 2A, a second group was fitted with four collars each of formulation 2B and the third group fitted with four collars each of formulation 2C. One collar was randomly removed from each dog on days 7, 14, 21 and 28 and analyzed to determine the percent change of the amount of TLM and TPP in the collar on the days stated.

In view of the substantially straight line release of TLM and TPP, a more efficient use of the active ingredient (TLM) is achieved. This is in sharp contrast to prior art release systems (blends) which give a bell curve release rate of the active ingredient and, consequently, inefficient use of the active ingredient. Because of the straight line rate of release of active ingredient by the systems of the present invention, it is possible to deliver a predetermined dose of active ingredient on a daily basis over a long period of time.

EXAMPLE 3

The following formulations can be used for cattle ear tags for very effective control of horn flies (percent by weight).

|  | A | B |
|---|---|---|
| TPP | 25.0 | 25.0 |
| TLM | 4.0 | 1.6 |
| PVC (high mol. wt.) | 47.5 | 49.9 |
| Stabilizer (CZ19A) | 0.5 | 0.5 |
| Epoxidized oil | 5.0 | 5.0 |
| Dioctyl adipate | 18.0 | 18.0 |

EXAMPLE 4

The following formulation was prepared for dog collars (percent by weight).

| PVC (med. mol. wt.) | 40.50 |
|---|---|
| Stabilizer (Witco CZ19A) | .50 |
| Epoxidized soybean oil | 5.00 |
| Diisooctyl adipate | 18.00 |
| TPP | 31.45 |
| Deltamethrin Tech. 98.4% | 3.05 |
| PMS 355T | 1.50 |

The formulation was blended by charging a ribbon blender with the PVC, stabilizer, EPO and the DIOA, heating to about 150 degrees F., and blending until a dry and flowable blend is obtained. TPP is added and blended until uniform. Deltamethrin is then uniformly added and the batch blended until dry and flowable. Heat is turned off and after cooling, pigment is added. The batch is extruded at about 300 degrees F. into collars. It is believed that in this procedure that the temperature of the blending effectively causes blending of the AI (deltamethrin) with TPP.

EXAMPLE 5

Emulsifiable Concentrate

|  | Percentages | |
|---|---|---|
|  | A | B |
| Dipropylene methyl ether | 76.0 | 70.0 |
| Deltamethrin 98.4% | 5.0 | 5.0 |
| Phosphage ester - Monafax 785 | 2.0 | 2.5 |
| Phosphate ester - Monafax 786 | 2.0 | 2.5 |
| Triphenyl phosphate | 15.0 | 20.0 |

EXAMPLE 6

Ready-To-Use (RTU) Horse Spray for flies

|  | Percentages | |
|---|---|---|
|  | A | B |
| Isopropyl alcohol | 93.9 | 93.4 |
| Deltamethrin 98.4% | 0.1 | 0.1 |
| Phosphate ester - Monafax 785 | 0.5 | 0.5 |
| Dipropylene methyl ether | 5.0 | 5.0 |
| Triphenyl phosphate | 0.5 | 1.0 |

EXAMPLE 7

Dip Small Animal (RTU) for fleas and ticks

|  | Percentages | |
|---|---|---|
|  | A | B |
| Dipropylene methyl ether | 5.0 | 5.0 |
| Distilled water | 92.99 | 92.49 |
| Monafax 785 | .50 | .50 |
| Monafax 786 | .50 | .50 |
| d-trans allethrin 94% | .11 | .11 |
| Piperonyl butoxide | .40 | .40 |
| Triphenyl phosphate | .50 | 1.00 |

EXAMPLE 8

Spot-On Small Animal for fleas and ticks

|  | Percentages | |
|---|---|---|
|  | A | B |
| Isopropyl alcohol | 40.0 | 20.0 |
| Permethrin | 20.0 | 20.0 |
| Dipropylene methyl ether | 20.0 | 20.0 |
| Triphenyl phosphate | 20.0 | 40.0 |

EXAMPLE 9

Granules—Lawn and Turf for cutworms, ants

|  | Percentages |
|---|---|
| Corncob grits | 85.94 |
| Tralomethrin 27.7% | .36 |
| Soybean oil | 10.00 |
| BHT | .10 |
| Triphenyl phosphate | 3.60 |

EXAMPLE 10

Dust—Small Animal for fleas and ticks

|  | Percentages |
|---|---|
| Calcium silicate - Micro Cel E | 17.9 |
| Kaolin - Borden AG-1 | 71.6 |
| Deltamethrin | .5 |
| Triphenyl phosphate | 10.0 |

EXAMPLE 11

Cattle Dust for flies and ticks

|  | Percentages |
|---|---|
| Polyvinyl chloride | 44.0 |
| Diisooctyl adipate | 20.0 |
| Epoxidized soybean oil | 3.0 |
| Alphamethrin | 3.0 |

| -continued | |
|---|---|
| | Percentages |
| Triphenyl phosphate | 30.0 |

In the polymeric pest control systems of the present invention, polymers conventionally employed in pest control strips, collars and ear tags can be used. These include polymers and copolymers of vinyl monomers such as vinyl chloride, vinyl acetate, acrylates and the like. Polymers described in U.S. Pat. Nos. 3,318,769 and 3,852,416, the disclosures of which are incorporated herein by reference, are suitable for use in the present invention.

The solvating plasticizer used in the polymeric pest control systems of the present invention are liquid plasticizers conventionally employed in polymeric pest control systems. These include the phthalic esters such as dioctyl phthlate, adipic esters such as dioctyl adipate, and the like.

The pest control systems of the present invention can use either a liquid or solid pest control agent or combinations thereof. The pest control agent can be an insecticide and/or acaricide. There can be included one or more pest control agents such as a natural or synthetic pyrethroid, a carbamate, a phosphate, a phosphorothioate, etc. For example, pyrethrin, allethrin, resmethrin, deltamethrin, tralomethrin, carbaryl, propoxur, dichlorvos, naled, diazinon, and the like. Preferred pest control active ingredients are the pyrethrins and synthetic pyrethroids.

Triphenyl phosphate is insoluble in water and a solid at room temperature. In preparing formulations of the present invention, TPP can be melted (49–50degrees C.) or a solution thereof in organic solvent and the AI pre-mixed therewith. Suitable organic solvents include ketones, ethers and alcohols.

The term "pest", as used herein, means insects and arachnids. All percentages herein are by weight.

What is claimed Is:

1. A method for reducing the irritation to warm blooded animals of a pest control active ingredient of a solid or liquid pest control active ingredient formulation which consists essentially of incorporating triphenyl phosphate into said formulation in an amount effective to reduce the irritation of said active ingredient to warm blooded animals, the amount of triphenyl phosphate being at least equal to the amount of active ingredient, said active consisting of pyrethrins and synthetic pyrethroids.

2. The method according to claim 1 wherein the amount of triphenyl phosphate is not less than double the amount of active ingredient, by weight.

3. The method according to claim 1 wherein the active ingredient is tralomethrin.

4. The method according to claim 1 wherein the active ingredient is deltamethrin.

5. The method according to claim 1 wherein the active ingredient is permethrin.

6. The method according to claim 1 wherein the active ingredient is a pyrethrin.

7. The method according to claim 1 wherein the formulation is a solid formulation selected from the group consisting of a vinyl polymer or copolymer, granules and dusts.

8. The method according to claim 7 wherein the polymer is a vinyl polymer or copolymer, said polymer being loaded with a highly solvating liquid plasticizer.

9. The method according to claim 7 wherein the formulation is a granule.

10. The method according to claim 7 wherein the formulation is a dust.

11. The method according to claim 1 wherein the formulation is an organic solvent liquid formulation or an aqueous and organic solvent liquid formulation.

12. The method according to claim 1 wherein the triphenyl phosphate is pre-blended with the active ingredient prior to incorporation into said formulation.

* * * * *